United States Patent
Rohde et al.

(10) Patent No.: US 9,394,212 B2
(45) Date of Patent: Jul. 19, 2016

(54) PROCESS FOR THE COOLIGOMERIZATION OF OLEFINS

(75) Inventors: Wolfgang Rohde, Speyer (DE); Qiang Miao, Worms (DE); Stefan Bitterlich, Dirmstein (DE); Gauthier Luc Maurice Averlant, Frankfurt (DE); Hans-Guenter Wagner, Neuleiningen (DE); Beatrice Rößler-Feigel, Weisenheim am Sand (DE)

(73) Assignee: BASF SE, Ludwigshafen (DE)

( * ) Notice: Subject to any disclaimer, the term of this patent is extended or adjusted under 35 U.S.C. 154(b) by 1081 days.

(21) Appl. No.: 13/159,761

(22) Filed: Jun. 14, 2011

(65) Prior Publication Data

US 2011/0306812 A1   Dec. 15, 2011

Related U.S. Application Data

(60) Provisional application No. 61/354,731, filed on Jun. 15, 2010.

(51) Int. Cl.
*C07C 2/00* (2006.01)
*C07C 2/12* (2006.01)

(52) U.S. Cl.
CPC ............. *C07C 2/12* (2013.01); *C07C 2523/755* (2013.01); *C07C 2529/072* (2013.01); *C07C 2529/70* (2013.01); *Y02P 20/582* (2015.11)

(58) Field of Classification Search
CPC ......................... C07C 2/00–2/12; C10G 50/00
USPC ......... 585/502, 510, 517, 520, 530, 531, 532, 585/533
See application file for complete search history.

(56) References Cited

U.S. PATENT DOCUMENTS

| | | | |
|---|---|---|---|
| 3,485,887 A | 12/1969 | Kronig et al. | |
| 4,517,395 A | 5/1985 | Obenaus et al. | |
| 5,220,088 A * | 6/1993 | Fujiwara et al. | 585/511 |
| 5,849,972 A | 12/1998 | Vicari et al. | |
| 6,660,898 B1 * | 12/2003 | Pyhälähti et al. | 585/510 |
| 7,259,285 B1 | 8/2007 | Walter et al. | |
| 7,476,773 B2 | 1/2009 | Louret et al. | |
| 8,129,572 B2 * | 3/2012 | Sigl et al. | 568/909 |
| 2007/0191661 A1 * | 8/2007 | Brown et al. | 585/517 |
| 2009/0312583 A1 | 12/2009 | Sigl et al. | |
| 2010/0190869 A1 | 7/2010 | Teles et al. | |
| 2010/0191018 A1 | 7/2010 | Teles et al. | |
| 2011/0124809 A1 | 5/2011 | Mijolovic et al. | |
| 2011/0130514 A1 | 6/2011 | Mijolovic et al. | |
| 2011/0144259 A1 | 6/2011 | Mijolovic et al. | |
| 2011/0178239 A1 | 7/2011 | Mijolovic et al. | |
| 2011/0218323 A1 | 9/2011 | Dahmen et al. | |

FOREIGN PATENT DOCUMENTS

| | | |
|---|---|---|
| DE | 1568542 | 5/1970 |
| DE | 43 39 713 A1 | 5/1995 |
| DE | 198 45 857 A1 | 4/2000 |
| DE | 199 57 173 A1 | 5/2001 |
| EP | 0 081 041 B1 | 1/1986 |
| EP | 1 739 069 A1 | 1/2007 |
| WO | WO 95/14647 A1 | 6/1995 |
| WO | WO 99/25668 A1 | 5/1999 |
| WO | WO 01/83407 A1 | 11/2001 |
| WO | WO 2007/040812 A1 | 4/2007 |
| WO | WO 2007/141288 A1 | 12/2007 |

OTHER PUBLICATIONS

Edgar, et al., "Process Control" in Perry's Chemical Engineers Handbook, McGraw-Hill, 7th ed., 1997, R. H. Perry and D. W. Green, eds., pp. 8-50 to 8-51—available on-line Mar. 2001.*
U.S. Appl. No. 13/479,961, filed May 24, 2012, Stroefer, et al.
Susann Albrecht et al., "Oligomerisierung Von N-Butenen", Chemie Ingenieur Technik, 2005, 15 Pages.
Bálint Heil et al. "Einfluβ Der Olefinstruktur Auf Die Reaktionsgeschwindigkeit", Chem. Ber., vol. 102, Jan. 27, 1969, pp. 2238-2240.
D. Commereuc et al., "Aspects Chimiques Du Procédé Dimersol De Dimérisation Des Oléfines", Revue De l'Institut Francais Du Petrole, vol. 37, No. 5, 1982, pp. 639-649.
F. Nierlich et al., "Oligomerize for Better Gasoline", Hydrocarbon Processing, Feb. 1992, pp. 45-46.
C. T. O'Connor, "Alkene Oligomerization", Catalysis Today, 1990, pp. 329-349.

* cited by examiner

*Primary Examiner* — In Suk Bullock
*Assistant Examiner* — Ali Z Fadhel
(74) *Attorney, Agent, or Firm* — Oblon, McClelland, Maier & Neustadt, L.L.P

(57) ABSTRACT

In a process for the cooligomerization of olefins, an olefin starting material comprising olefins having n carbon atoms and olefins having 2n carbon atoms is reacted over an olefin oligomerization catalyst to give a reaction product. The process is carried out under such conditions that the conversion of olefins having 2n carbon atoms is less than 10%. Both the cooligomer having 3n carbon atoms and the olefin having 2n carbon atoms which has been separated off from the reaction product have a high hydroformylatability.

18 Claims, No Drawings

PROCESS FOR THE COOLIGOMERIZATION OF OLEFINS

The invention relates to a process for the cooligomerization of olefins, in which an olefin starting material comprising olefins having n carbon atoms and olefins having 2n carbon atoms is reacted over an olefin oligomerization catalyst.

Short-chain olefins can be obtained on a large industrial scale. Thus, for example, a hydrocarbon mixture referred to as $C_4$ fraction which has a high total olefin content and in which the olefins are essentially olefins having 4 carbon atoms is obtained in the processing of petroleum by steam cracking or fluid catalytic cracking (FCC).

Higher olefins are frequently obtained by oligomerization of lower, monomeric olefins. The oligomerization is carried out over homogeneous or heterogeneous catalysts. Such catalysts can be divided into two large classes, viz. acid catalysts and coordinative catalysts. The first class includes zeolites in the H form, and the latter includes, for example, nickel oxide-based catalysts. In the case of unsymmetrical olefin monomers, the structure of the product depends essentially on which of the two different carbon atoms of the double bond of the monomer chain growth occurs. Thus, more or less strongly branched olefinic oligomers having more or less highly substituted double bonds are formed. Since the olefinic oligomers can in turn react with themselves or with further monomer and a shift of the double bonds can also occur, the oligomerization of olefin monomers is highly complex and generally cannot be described fully. An overview may be found in S. Albrecht et al., Chemie Ingenieur Technik, 77, 695 (2005).

A plurality of products which differ in the degree of oligomerization, i.e. in the chain length or number of carbon atoms, are therefore always obtained. The various oligomers are generally separated into fractions according to the number of carbon atoms present therein and passed to various applications. The oligomers having the same number of carbon atoms are in turn complex mixtures of various isomers.

To increase the selectivity to oligomers higher than dimers, mixtures of monomers and dimers can also be used as starting material for the oligomerization instead of pure monomer. Here, a homodimerization of the monomer usually takes place in addition to the codimerization of dimer and monomer. Pure monomer is usually oligomerized in a first reaction unit and monomers and oligomers are reacted with one another in one or more subsequent reaction units.

WO 01/83407 discloses a process for the oligomerization of alkenes having from 3 to 6 carbon atoms, in which a feed comprising (a) alkenes having x carbon atoms and (b) optionally alkenes having y carbon atoms (where x and y are different) is brought into contact with an MFS zeolite catalyst. The conditions are selected so that an oligomeric product having major proportions of particular oligmers is selectively obtained.

WO 2007/040812 describes a process for converting lower olefins into higher olefins, in which a feed comprising a $C_3$-$C_5$-olefin monomer and a dimer of the monomer is brought into contact with a zeolite oligomerization catalyst and a trimer of the olefin monomer is obtained.

WO 2007/141288 describes a process for the codimerization of olefins, in which a first olefin starting material which consists essentially of $C_n$-olefins and a second olefin starting material which consists essentially of $C_m$-olefins, where n and m are independently of one another two different integers from 2 to 12, is provided and the first olefin starting material and the second olefin starting material are reacted over a heterogeneous olefin oligomerization catalyst, in particular an olefin oligomerization catalyst based on a sheet and/or framework silicate.

EP-A 1739069 describes the production of a diesel fraction, in which a $C_2$-$C_{12}$-olefinic hydrocarbon fraction is oligomerized, the mixture obtained is separated into a light fraction comprising unreacted $C_4$- and/or $C_5$-olefinic hydrocarbons, a middle fraction and a heavy fraction, and the middle fraction is oligomerized with the light fraction in a weight ratio of 60:40-80:20.

If olefin isomer mixtures are used for the oligomerization, the more reactive isomers generally preferentially react first. Severe depletion of the reaction mixture in reactive isomers can occur before the less reactive olefins also participate in the oligomerization. Since the oligomerization reaction is usually carried out to partial conversion, in the extreme case entirely unreacted less reactive olefins can be recovered in the reaction discharge.

The olefinic oligomers obtained are then frequently converted by hydroformylation into the alcohols having, in each case, one more carbon atom (oxo alcohols), which in turn represent important base products for plasticizers and surfactants. The hydroformylatability of an olefin (i.e. the reaction rate of the hydroformylation under defined conditions determined by conventional methods) depends on the degree of branching of the olefin to be hydroformylated and the degree of substitution of the olefinic double bonds. According to B. Heil et al. (Chem. Ber., 102, 2238-2240 (1969)), the hydroformylatability of olefins decreases in the following order: linear $\alpha$-olefins>linear internal olefins>branched olefins, in particular those having substituted double bonds.

It is an object of the invention to provide a process for the cooligomerization of olefins, in which an olefin starting material comprising olefins having n carbon atoms and olefins having 2n carbon atoms is reacted over an olefin oligomerization catalyst to give a reaction product and in which both the cooligomer having 3n carbon atoms and the olefin having 2n carbon atoms separated off from the reaction product have a hydroformylatability which is as high as possible.

The object is achieved by a process for the cooligomerization of olefins, wherein an olefin starting material comprising olefins having n carbon atoms and olefins having 2n carbon atoms is reacted over an olefin oligomerization catalyst to give a reaction product and the process is carried out under such conditions that the conversion of olefins having 2n carbon atoms is less than 10%.

The coefficient n is an integer from 3 to 10, preferably from 4 to 6.

In the cooligomerization, (a) olefins having 2n carbon atoms are converted into olefins having 3n and/or more carbon atoms and, simultaneously, (b) olefins having n carbon atoms are dimerized to form olefins having 2n carbon atoms. The conversion (or net conversion) of olefins having 2n carbon atoms is the difference between the amount of olefins having 2n carbon atoms consumed according to (a) and the amount of olefins having 2n carbon atoms formed according to (b). If the amount of olefins having 2n carbon atoms formed according to (b) is greater than the amount of olefins having 2n carbon atoms consumed according to (a), there is a negative conversion, i.e. a net formation of olefins having 2n carbon atoms.

The process of the invention operates at a conversion of olefins having 2n carbon atoms of less than 10%, preferably less than 5%, in particular about 0%, or at a negative conversion. If the conversion is negative, its absolute value is preferably less than 25%.

The conversion of olefins having 2n carbon atoms when the process is carried out continuously can be established by comparing the mass flow of olefins having 2n carbon atoms in the reaction product leaving the process with the mass flow of olefins having 2n carbon atoms in the starting material fed to the process. The mass flow is expressed as mass per unit time or moles per unit time. The conversion is based on the mass flow of olefins having 2n carbon atoms in the starting material fed to the process. According to the invention, the mass flow of olefins having 2n carbon atoms leaving the process is greater than 90% of the mass flow of olefins having 2n carbon atoms fed in.

The process of the invention can therefore advantageously be regulated by measuring at least one control parameter which describes the net conversion of olefins having 2n carbon atoms and making adjustments to regulate the control parameter, for example, at least one control parameter is the amount of olefins having 2n carbon atoms in the reaction product. This amount is determined either by analytical methods known to those skilled in the art, e.g. on-line GC, or by measuring the amount of the corresponding fraction which is obtained in the fractional distillation following the reaction. It is of course possible to measure further control parameters. As correcting variable, use is made, for example, of at least one parameter selected from the residence time of the olefin starting material over the olefin oligomerization catalyst, the mass flow of the olefin starting material, the mass flow of a recycle or circulation stream which is optionally present, the ratio of olefins having n carbon atoms to olefins having 2n carbon atoms in the olefin starting material and the reaction temperature at the reactor inlet and the reactor outlet.

Regulation can be carried out by means of computer-based process control. In a control unit, the influence of the change in a correcting variable on one or more control parameters can be stored as a mathematical model or algorithm. The measured values of one or more control parameters are used to determine adjustments for regulating the control parameter. Suitable models and programs which can be employed for implementing the present invention will be familiar to a person skilled in the art. In the simplest case, regulation is carried out manually by the operator adjusting appropriate correcting variables on the basis of a change in the control parameter.

The molar ratio of olefins having n carbon atoms to olefins having 2n carbon atoms is in the range from 1:10 to 20:1, preferably in the range from 1:4 to 8:1, particularly preferably in the range from 1:2 to 4:1, in particular in the range from 1:1 to 2.5:1.

The reaction product obtained can be separated into a fraction comprising unreacted olefins having n carbon atoms, olefins having 2n carbon atoms, olefins having 3n carbon atoms and optionally higher-boiling fractions in a conventional manner, e.g. by distillation. The olefins having 2n carbon atoms and olefins having 3n carbon atoms can be passed to various uses, e.g. hydroformylation.

In a specific embodiment, the reaction product is divided into a first substream and a second substream, with the first substream being subjected to a work-up and the second substream being recirculated. This recirculated substream can be cooled beforehand by indirect heat exchange.

In a specific variant, an olefin-comprising stream which has been obtained in the work-up of the reaction product or of the first substream of the reaction product is additionally fed into the reaction system.

Olefins having 3n carbon atoms which have been separated off from the reaction product can, if desired, be transferred together with olefins having n carbon atoms to a further cooligomerization which is carried out under such conditions that the mass flow of olefins having 3n carbon atoms leaving the further cooligomerization is greater than 90% of the mass flow of olefins having 3n carbon atoms fed in.

To avoid secondary reactions and to achieve better removal of the heat of reaction, the process is preferably carried out in a plurality of stages, in each case with partial conversion of the olefins having n carbon atoms. The process is preferably carried out under such conditions that the conversion of the olefins having n carbon atoms in each individual stage is in the range from 5 to 50%. Here, the conversion is defined as the difference between the mass flows of all olefinic hydrocarbons having n carbon atoms in the feed to and in the discharge from the reactor divided by the mass flow of the olefinic hydrocarbons having n carbon atoms in the feed.

Preferred olefins having n carbon atoms are in principle all compounds which have from 3 to 10 carbon atoms, preferably from 4 to 6 carbon atoms, and at least one ethylenically unsaturated double bond. The olefins used are preferably selected from linear (straight-chain) olefins and olefin mixtures comprising at least one linear olefin. These include propene, 1-butene, 2-butene, 1-pentene, 2-pentene, 1-hexene, 2-hexene, 3-hexene and mixtures thereof.

Preference is given to using an industrially available olefin-comprising hydrocarbon mixture as olefin starting material having n carbon atoms. Here, the monomeric olefin starting material can generally comprise not only olefins but also saturated hydrocarbons, predominantly hydrocarbons having the same number of carbon atoms in each case. Such olefin feed streams are frequently obtained as cracker products, e.g. as C4 or C5 fractions or the raffinates obtained therefrom.

A preferred source of olefins having n carbon atoms is industrially available olefin mixtures resulting from hydrocarbon cracking in petroleum processing, for example by catalytic cracking such as fluid catalytic cracking (FCC), thermocracking or hydrocracking followed by dehydrogenation. One suitable industrial olefin mixture is a $C_4$ fraction. $C_4$ fractions can be obtained, for example, by fluid catalytic cracking or steam cracking of gas oil or by steam cracking of naphtha. Depending on the composition of the $C_4$ fraction, a distinction is made between the total $C_4$ fraction (crude $C_4$ fraction), the raffinate I obtained after 1,3-butadiene has been separated off and the raffinate II obtained after isobutene has been separated off. A further suitable industrial first olefin mixture is the $C_5$ fraction which can be obtained in the cracking of naphtha. Suitable olefin-comprising hydrocarbon mixtures having from 4 to 6 carbon atoms can also be obtained by catalytic dehydrogenation of suitable industrial available paraffin mixtures. Thus, for example, $C_4$ olefin mixtures can be produced from liquefied petroleum gas (LPG) and liquefied natural gas (LNG). The latter comprises not only the LPG fraction but also relatively large amounts of relatively high molecular weight hydrocarbons (light naphtha) and is thus also suitable for producing $C_5$- and $C_6$-olefin mixtures. The production of olefin-comprising hydrocarbon mixtures comprising monoolefins having from 4 to 6 carbon atoms from LPG or LNG streams is carried out by customary processes which are known to those skilled in the art and comprise not only dehydrogenation but generally also one or more work-up steps. These include, for example, the removal of at least part of the saturated hydrocarbons comprised in the abovementioned olefin feed mixtures. These can, for example, be reused for producing olefin starting materials by cracking and/or dehydrogenation. However, the olefins used in the process of the invention can also comprise a proportion of saturated hydrocarbons which are inert under the oligomerization conditions used according to the invention. The proportion of these saturated components is generally not more than 60% by weight, preferably not more than 40% by weight, particularly preferably not more than 30% by weight, based on the total amount of olefins and saturated hydrocarbons comprised in the hydrocarbon starting material.

A raffinate II suitable for use in the process of the invention has, for example, the following composition:
from 0.5 to 5% by weight of isobutane,
from 5 to 30% by weight of n-butane,
from 20 to 40% by weight of trans-2-butene,
from 10 to 20% by weight of cis-2-butene,
from 25 to 55% by weight of 1-butene,
from 0.5 to 5% by weight of isobutene
and also trace gases such as 1,3-butadiene, propene, propane, cyclopropane, propadiene, methylcyclopropane, vinylacetylene, pentenes, pentanes, etc. in the range in each case of not more than 1% by weight.

If diolefins or alkynes are present in the olefin-rich hydrocarbon mixture, these can be removed therefrom down to a level of preferably less than 200 ppm per weight before the oligomerization. They are preferably removed by selective hydrogenation, e.g. as described in EP-81 041 and DE-15 68 542, particularly preferably by means of a selective hydrogenation down to a residual content of less than 100 ppm by weight, in particular 10 ppm by weight.

In addition, oxygen-comprising compounds such as alcohols, aldehydes, ketones or ethers are advantageously largely removed from the olefin-rich hydrocarbon mixture. For this purpose, the olefin-rich hydrocarbon mixture can advantageously be passed over an adsorbent, e.g. a molecular sieve, preferably an adsorbent as described in DE-A-19845857, which is hereby incorporated by reference. The concentration of oxygen-comprising, sulfur-comprising, nitrogen-comprising and halogen-comprising compounds in the olefin-rich hydrocarbon mixture is preferably less than 20 ppm by weight, particularly preferably less than 10 ppm by weight, in particular less than 1 ppm by weight.

Olefins having 2n carbon atoms are preferably ones obtained by prior dimerization of olefins having n carbon atoms. Olefins having 2n carbon atoms are, in particular, olefins having 8 carbon atoms, i.e. octenes. The olefins used for the oligomerization are preferably selected from linear olefins and olefins having a low degree of branching and olefin mixtures. The $C_{2n}$-olefin mixture can also be subjected to a suitable purification to remove oxygen-, sulfur- or nitrogen-comprising compounds and also conjugated multiply unsaturated olefins before introduction into the cooligomerization reactor. $C_{2n}$-olefin mixtures can comprise small amounts of dissolved oxygen due to their method of production and this can also be removed by means of suitable absorptive or chemical, in particular catalytic, measures known to those skilled in the art in order to protect the oligomerization catalyst.

Suitable octenes are, for example, 1-octene, 2-octene, 3-octene, 4-octene, 2-methyl-hept-1-ene, 2-methyl-hept-2-ene, 2-methyl-hept-3-ene, 6-methyl-hept-3-ene, 6-methyl-hept-2-ene, 6-methyl-hept-1-ene, 3-methyl-hept-1-ene, 3-methyl-hept-2-ene, 3-methyl-hept-3-ene, 5-methyl-hept-3-ene, 5-methyl-hept-2-ene, 5-methyl-hept-1-ene, 4-methyl-hept-1-ene, 4-methyl-hept-2-ene, 4-methyl-hept-3-ene and mixtures thereof.

Preferred industrially available $C_8$-olefin mixtures result, for example, in the DIMERSOL process, in which butene is oligomerized in the homogeneous phase in the presence of a catalyst system composed of a transition metal derivative and a metal-organic compound (Revue de l'Institut Français du Petrole, vol. 37, No. 5, September/October 1982, page 639ff). $C_8$-olefin mixtures suitable as second olefin starting material also result from the Octol process of Hüls AG (Hydrocarbon Processing, February 1992, pp. 45/46). Suitable processes for producing $C_8$-olefin mixtures having a low degree of branching are also described in DE-A-43 39 713 and WO 99/25668, which are hereby fully incorporated by reference. In a preferred embodiment, olefins having 2n carbon atoms are obtained by dimerization of a raffinate II, as defined above, in the presence of a nickel-comprising oligomerization catalyst.

A particularly preferred embodiment concerns a process in which (i) in a dimerization stage, an olefin starting material comprising olefins having n carbon atoms is reacted over a first olefin oligomerization catalyst to give a first reaction product,
olefins having 2n carbon atoms are isolated from the first reaction product, and (ii) in a cooligomerization stage, an olefin starting material comprises olefins having n carbon atoms and at least part of the olefins having 2n carbon atoms obtained in the dimerization stage is reacted over a second olefin oligomerization catalyst to give a second reaction product, where the cooligomerization is carried out under such conditions that the conversion of olefins having 2n carbon atoms is less than 10%.

Preference is given to at least the second olefin oligomerization catalyst being a nickel-comprising heterogeneous catalyst; in particular, the first olefin oligomerization catalyst and the second olefin oligomerization catalyst are each a nickel-comprising heterogeneous catalyst as described in more detail below.

The cooligomerization is preferably carried out continuously. For this purpose, the olefin starting material comprising olefins having n carbon atoms and olefins having 2n carbon atoms is fed into a reactor system and reacted over the olefin oligomerization catalyst.

The reaction system used in the process of the invention can comprise one or more, identical or different reactors. In the simplest case, the reaction system is formed by a single reactor. If a plurality of reactors are used, these can have identical or different mixing characteristics. The individual reactors can, if desired, be divided one or more times by internals. If two or more reactors form the reaction system, these can be connected with one another in any way, e.g. in parallel or in series. In a preferred embodiment, a reaction system comprising two reactors connected in series is used.

Suitable pressure-rated reaction apparatuses for the oligomerization are known to those skilled in the art. They include the generally customary reactors for gas-solid and gas-liquid reactions, e.g. tube reactors, stirred vessels, gas recycle reactors, bubble columns, etc., which can optionally be divided by internals. Preference is given to using shell-and-tube reactors or loop reactors which can be operated in the upflow mode or the downflow mode. In the reactor or reactors, the catalyst can be arranged in a single fixed catalyst bed or in a plurality of fixed catalyst beds. Here, it is possible to use different catalysts in the individual reaction zones. However, the use of the same catalyst in all reaction zones is preferred.

The temperature in the cooligomerization reaction is generally in the range from about 20 to 280° C., preferably from 25 to 200° C., in particular from 30 to 140° C. If the reaction system comprises more than one reactor, these can have identical or different temperatures. Likewise, a reactor can have a plurality of reaction zones which are operated at various temperatures. Thus, for example, the temperature set in a second reaction zone of an individual reactor can be higher than that in the first reaction zone or the temperature set in the second reactor of a reactor cascade can be higher than that in the first reactor, e.g. to achieve as complete as possible a conversion.

The pressure in the oligomerization is generally in the range from about 1 to 300 bar, preferably from 5 to 100 bar and in particular from 10 to 70 bar. When a plurality of reactors is used, the reaction pressure can be different in the individual reactors.

In general, the temperatures and pressures used for the oligomerization are selected so that the olefin-comprising starting material is present as a liquid or in the supercritical state.

In general, the olefinic components comprised in the reaction mixture can undergo not only oligomerization reactions but also isomerization reactions under the reaction conditions. These isomerizations predominantly involve shifting of the ethylenic double bond along the carbon chain, but skeletal isomerizations which lead to rearrangement of the carbon chain can also occur. The double bond isomerizations in particular proceed exothermically.

The oligomerization reaction also proceeds exothermically. The reaction can be carried out adiabatically or with removal of the heat of reaction by indirect heat exchange with an external heat transfer medium. Suitable apparatuses for heat exchange and for the removal of process heat are the customary apparatuses known to those skilled in the art. The heat exchange apparatus can be installed on or in the reactor.

The reaction is preferably carried out adiabatically. For the purposes of the present invention, this term is used in the industrial sense and not the physicochemical sense. While flowing through the reaction system, for example a catalyst bed, the reaction mixture experiences an increase in temperature. For the purposes of the present invention, adiabatic conditions refer to a procedure in which the quantity of heat liberated in an exothermic reaction is taken up by the reaction mixture in the reactor and no cooling by means of cooling devices is employed. Thus, the heat of reaction is removed from the reactor with the reaction mixture, apart from a proportion which is given off by the reactor to the environment by natural heat conduction and heat radiation. In such an adiabatic mode of operation, a continuous temperature profile in the flow direction is established in the respective reactor.

In the above-described process variant with recirculation of a substream of the reaction product, heat can be withdrawn from the substream by indirect heat exchange. The quantity of heat recovered can be reused at another point in the process, e.g. in the fractionation of the reaction product.

The olefin oligomerization catalyst is preferably a transition metal-comprising catalyst, in particular a heterogeneous catalyst. Suitable catalysts are known to those skilled in the art. They include the catalysts described in Catalysis Today, 6, 329 (1990), in particular pages 336-338, and in DE-A-43 39 713 (=WO-A 95/14647) and DE-A-199 57 173.

Preference is given to using an oligomerization catalyst comprising nickel. The heterogeneous nickel-comprising catalysts used can have various structures. Both all-active catalysts and supported catalysts are suitable in principle. The former are preferably used. The support materials can be, for example, silica, alumina, aluminosilicates, aluminosilicates having sheet structures and zeolites such as mordenite, faujasite, zeolite X, zeolite Y and ZSM-5, zirconium oxide which has been treated with acids or sulfated titanium dioxide. Precipitated catalysts which can be obtained by mixing of aqueous solutions of nickel salts and silicates, e.g. sodium silicate with nickel nitrate, and optionally aluminum salts such as aluminum nitrate and calcination are particularly suitable. Furthermore, it is possible to use catalysts obtained by intercalation of $Ni^{2+}$ ions into natural or synthetic sheet silicates such as montmorillonites by ion exchange. Suitable catalysts can also be obtained by impregnation of silica, alumina or aluminosilicates with aqueous solutions of soluble nickel salts such as nickel nitrate, nickel sulfate or nickel chloride, and subsequent calcination.

Catalysts comprising nickel oxide are preferred. Particular preference is given to catalysts which consist essentially of NiO, $SiO_2$, $TiO_2$ and/or $ZrO_2$ and optionally $Al_2O_3$. Greatest preference is given to a catalyst comprising, as significant active constituents, from 10 to 70% by weight of nickel oxide, from 5 to 30% by weight of titanium dioxide and/or zirconium dioxide, from 0 to 20% by weight of aluminum oxide and silicon dioxide as balance. Such a catalyst can be obtained by precipitation of the catalyst composition at pH 5-9 by addition of an aqueous solution comprising nickel nitrate to an alkali metal water glass solution comprising titanium dioxide and/or zirconium dioxide, filtration, drying and heat treatment at from 350 to 650° C. For details of the production of these catalysts, reference may be made to DE-43 39 713. The disclosure of this document and the prior art cited therein is fully incorporated by reference.

In a further embodiment, a nickel catalyst as described in DE-A-199 57 173 is used as catalyst. This is essentially aluminum oxide which has been treated with a nickel compound and a sulfur compound. The molar ratio of sulfur to nickel in the finished catalyst is preferably in the range from 0.25:1 to 0.38:1.

The catalyst is preferably present in shaped form, e.g. in the form of pellets, e.g. having a diameter of from 1.5 to 6 mm and a height of from 1.5 to 6 mm, rings having, for example, an external diameter of from 5 to 7 mm, a height of from 2 to 5 mm and a hole diameter of from 2 to 3 mm or extradites of various lengths having a diameter of, for example, from 1.5 to 5 mm. Such shapes are obtained in a manner known per se by tableting, usually with use of a tableting aid such as graphite or stearic acid, or by extrusion.

In a less preferred embodiment, the olefin oligomerization catalyst comprises at least one zeolite or consists of at least one zeolite.

Suitable zeolites have an average pore diameter of at least 5 Å, particularly preferably at least 6 Å, in particular at least 7 Å.

Suitable zeolites are selected from the following structure types (designation follows the nomenclature of the International Zeolite Association): BEA, MFI, MEL, FAU, MOR, MWW, LTL, LTA, CHA, TON, MTW, FER, MAZ, EPI and GME.

The zeolites used can, for example, be used in the $H^+$, ammonium, alkali metal or alkaline earth metal form.

The zeolites used can be subjected to at least one modification step before being used for the olefin oligomerization. Such steps include, for example, modification by means of acids, ammonium salt solutions and/or metal salt solutions. Further examples are dealumination of the aluminum built into the silicate framework, dehydroxylation, extraction of "extra-framework" aluminum oxide or silylation. The olefin oligomerization catalyst can also be subjected to modification by shaping, thermal treatment or treatment with water vapor (steaming). Such a modification makes it possible to achieve the highest possible selectivity, high conversions, long catalyst operating lives and/or a large number of possible regeneration cycles.

In one embodiment of the process of the invention, a zeolite in the $H^+$ form is used as olefin oligomerization catalyst.

The invention is illustrated by the following examples.

COMPARATIVE EXAMPLE 1 AND EXAMPLES 2 AND 3

In examples 1 and 2, butene (raffinate II having the following composition: 7.1% by weight of isobutane, 19.3% by weight of n-butane, 19.9% by weight of trans-2-butene, 41.6% by weight of 1-butene, 9.5% by weight of cis-2-butene and 2.6% by weight of isobutene) is oligomerized with octane which had been obtained beforehand in a first reaction unit by oligomerization of raffinate II over an NiO-based catalyst (EP 730567 B, example 1), over a zeolitic acid catalyst based on an H-MWW zeolite (molar ratio of the elements Si:Al:Fe 27:1:0.07, extruded with 20% of boehmite as binder) to form dodecene. The molar ratio of $C_4$:$C_8$ was in each case 2:1. The reaction was carried out in a continuously operated reactor having a diameter of 29.7 mm and a total length of 3 m at 90° C. and the weight hourly space velocity (WHSV) indicated in the table below.

In example 3, the same reaction was carried out using a molar ratio of C4- to C8-olefins of 1:1 in the feed stream over an NiO-based catalyst as had been used for the preparation of octene.

The product formed is fractionally distilled and the dodecene obtained in this way is hydroformylated. For this purpose, an autoclave is charged with 1200 g of dodecene. The autoclave is then pressurized to 220 bar with a $CO/H_2$ mixture (1:1) and heated to 185° C. 9.6 g of cobalt ethylhexanoate dissolved in about 100 g of dodecene are then introduced into the reactor via a lock. The consumption of synthesis gas, indicated by a pressure drop in the autoclave, was replaced by injection of further amounts. To determine the hydroformylatability, a sample is taken after 60 minutes and analyzed by gas chromatography.

| | | Cooligomerization | | | Hydro- |
|---|---|---|---|---|---|
| | | | Conver- | Conver- | formyl- |
| | | Temper- | sion | sion | ation |
| Exam- | | WHSV | ature | C4 | C8 | conversion |
| ple | Catalyst | 1/h | ° C. | % | % | % |
| 1 | H-MWW | 0.4 | 90 | 54 | 11 | 55 |
| 2 | H-MWW | 1.6 | 90 | 35 | 3 | 61 |
| 3 | NiO | 1.1 | 90 | 38 | −4 | 81 |

It can be seen that when using the same catalysts, the hydroformylatability of dodecene increases significantly with decreasing C8 conversion. Furthermore, it can be seen that in the case of the preferred use of identical catalysts in the C4 dimerization and in the codimerization of C4- and C8-olefins at a low C8 conversion (here<0%), particularly readily hydroformylatable dodecene can be obtained.

COMPARATIVE EXAMPLES 4 AND 5 AND EXAMPLES 6 TO 8

In the following examples, a feed mixture of C4- and C8-olefins is reacted as described in example 3 over an NiO-based catalyst (corresponding to EP 730567 B, example 1) at 95° C. and various throughputs. Samples were taken for each setting and worked-up by distillation to separate the C8- and C12-olefins. The C8- and C12-olefin fractions obtained in pure form in this way were in each case subjected to a hydroformylation as follows:

100 g of dodecene (octene) were reacted batchwise in an autoclave using 0.13% by weight of Co ethylhexanoate as catalyst with addition of 10 g of water at 175° C. (160° C.) and under a synthesis gas pressure of 280 bar at a mixing ratio of $CO:H_2$ of 1:1 for 4 hours. The consumption of synthesis gas, indicated by a pressure drop in the autoclave, was replaced by injection of further amounts. After venting of the autoclave, the reaction discharge was treated with 10% strength by weight acetic acid and freed oxidatively of cobalt catalyst by passing in of air and the organic product phase was hydrogenated using Raney nickel at 170° C. and a hydrogen pressure of 280 bar. The analysis of the product mixture obtained was carried out by gas chromatography.

| | Cooligomerization | | | Hydro-formyl-ation | Hydro-formyl-ation | Average hydro-formyl- |
|---|---|---|---|---|---|---|
| | | Conver-sion | Conver-sion | ation conver- | conver-sion | ation conver- |
| Exam-ple | WHSV 1/h | C4 % | C8 % | sion C8 % | C12 % | sion % |
| 4 | 0.15 | 43 | 17 | 97.9 | 79.5 | 88.7 |
| 5 | 0.37 | 37 | 15 | 95.9 | 80.1 | 88.0 |
| 6 | 0.67 | 28 | 4 | 95.9 | 85.7 | 90.8 |
| 7 | 1.34 | 23 | 1 | 98.3 | 88.4 | 93.4 |
| 8 | 2.24 | 21 | 0 | 98.1 | 86.3 | 92.2 |

It can be seen here that at a high C8 conversion, a ready hydroformylatable octene but no readily hydroformylatable dodecene is obtained. Only at low C8 conversions of less than 10% are both products readily hydroformylatable, which is made clear by averaging the hydroformylation conversions of the C8- and C12-olefin.

The invention claimed is:

1. A process for the cooligomerization of olefins, comprising reacting an olefin starting material comprising olefins having n carbon atoms and olefins having 2n carbon atoms over an olefin oligomerization catalyst to give a reaction product, wherein the process is carried out so that the net conversion of olefins having 2n carbon atoms is non-negative and less than 5%; a conversion of olefins having n carbon atoms is in a range of from 10 to 50%; and n is an integer from 3 to 10.

2. The process according to claim 1, wherein the net conversion of olefins having 2n carbon atoms is less than or equal to 1%.

3. The process according to claim 1, wherein a part of the reaction product is cooled by indirect heat exchange and recirculated to the olefin starting material.

4. The process according to claim 1, wherein a nickel-comprising heterogeneous catalyst is the olefin oligomerization catalyst.

5. The process according to claim 1, wherein a zeolitic heterogeneous catalyst is the olefin oligomerization catalyst.

6. The process according to claim 1, wherein the amount of olefins having 2n carbon atoms in the reaction product obtained is regulated by targeted setting of at least one correcting variable.

7. The process according to claim 6, wherein the correcting variable is at least one parameter selected from the group consisting of residence time of the olefin starting material over the olefin oligomerization catalyst, the mass flow of the olefin starting material, the mass flow of a recycle or circulation stream, the ratio of olefins having n carbon atoms to olefins having 2n carbon atoms in the olefin starting material and the reaction temperature.

8. The process according to claim 1, which comprises an upstream dimerization stage in which said olefin starting material comprising olefins having n carbon atoms is reacted over said olefin oligomerization catalyst to form olefins having 2n carbon atoms.

9. The process according to claim 1, wherein the olefins having n carbon atoms are n-butenes and the olefins having 2n carbon atoms are at least one olefin selected from the group consisting of 2-methyl-hept-1-ene, 2-methyl-hept-2-ene, 2-methyl-hept-3-ene, 6-methyl-hept-3-ene, 6-methyl-hept-2-ene, 6-methyl-hept-1-ene, 3-methyl-hept-1-ene, 3-methyl-hept-2-ene, 3-methyl-hept-3-ene, 5-methyl-hept-3-ene, 5-methyl-hept-2-ene, 5-methyl-hept-1-ene, 4-methyl-hept-1-ene, 4-methyl-hept-2-ene, 4-methyl-hept-3-ene and mixtures thereof.

10. The process according to claim 1, wherein, n is an integer from 4 to 6.

11. The process according to claim 1, wherein, the net conversion of olefins having 2n carbon atoms is about 0%.

12. The process according to claim 1, wherein a molar ratio of olefins having n carbon atoms to olefins having 2n carbon atoms is in a range from 1:10 to 20:1.

13. The process according to claim 1, wherein a molar ratio of olefins having n carbon atoms to olefins having 2n carbon atoms is in a range from 1:4 to 8:1.

14. The process according to claim 1, wherein a molar ratio of olefins having n carbon atoms to olefins having 2n carbon atoms is in a range from 1:2 to 4:1.

15. The process according to claim 1, wherein a molar ratio of olefins having n carbon atoms to olefins having 2n carbon atoms is in a range from 1:1 to 2.5:1.

16. The process according to claim 1, wherein said process is carried out in a plurality of stages.

17. The process according to claim 16, wherein a conversion of olefins having n carbon atoms in each individual stage is in a range from 5 to 50%.

18. The process according to claim 1, wherein the olefins having n carbon atoms are n-butenes and the olefins having 2n carbon atoms are at least one olefin selected from the group consisting of 1-octene, 2-octene, 3-octene, 4-octene, 2-methyl-hept-1-ene, 2-methyl-hept-2-ene, 2-methyl-hept-3-ene, 6-methyl-hept-3-ene, 6-methyl-hept-2-ene, 6-methyl-hept-1-ene, 3-methyl-hept-1-ene, 3-methyl-hept-2-ene, 3-methyl-hept-3-ene, 5-methyl-hept-3-ene, 5-methyl-hept-2-ene, 5-methyl-hept-1-ene, 4-methyl-hept-1-ene, 4-methyl-hept-2-ene, 4-methyl-hept-3-ene and mixtures thereof.

* * * * *